United States Patent [19]
Johnson

[11] Patent Number: 4,602,626
[45] Date of Patent: Jul. 29, 1986

[54] POST-SURGICAL FOOT SPLINT

[76] Inventor: J. Barry Johnson, 708 Lankashire Rd., Winston-Salem, N.C. 27106

[21] Appl. No.: 630,437

[22] Filed: Jul. 13, 1984

[51] Int. Cl.$^4$ ............................................. A61F 5/00
[52] U.S. Cl. .................................. 128/80 R; 128/83.5
[58] Field of Search ....................... 128/80 R, 82, 83.5

[56] References Cited
U.S. PATENT DOCUMENTS 3,584,402  6/1971  Silverman ..................... 128/83.5 X
4,446,856  5/1984  Jordan ............................... 128/83.5

Primary Examiner—John D. Yasko
Attorney, Agent, or Firm—Charles R. Rhodes; Judith E. Garmon

[57] ABSTRACT

A foot splint to be worn following surgery on the metatarsophalangeal area of the foot includes the sole having an upper foot supporting surface and a lower ground-engaging surface, and a leather upper which surrounds and embraces the foot and secures the sole in place. The foot supporting surface of the sole includes a recess or depression underlying a selected one of the metatarsal joints of the foot for floating the selected metatarsophalangeal joint or area. Other areas of the sole are formed with convex portions to place more pressure on the portions of the foot they support, thereby relieving pressure from the area where the surgery took place. In a preferred embodiment the ground-engaging surface of the sole includes an upwardly inclined area substantially underlying the ball and anterior portion of the foot and a substantially flat walking surface underneath the arch and posterior portion of the foot.

4 Claims, 7 Drawing Figures

POST-SURGICAL FOOT SPLINT

BACKGROUND AND SUMMARY OF THE PRESENT INVENTION

Following surgery to the foot, and particularly surgery to the metatarsophalangeal area, it is desirable to apply a splint to support the foot and prevent flexing of the operative joint. Various approaches have been attempted in the design of such splint, such approaches being directed to relieving the forward portion of the foot from flexing of the joint which would occur during walking.

One early approach to such type of device is disclosed in U.S. Pat. No. 2,725,648, a splint or "rocker" device which, in one embodiment, is attached to the undersole of a conventional shoe. The rocker is designed for use without a shoe and comprises a block of rigid material having a convex, arch-supporting upper surface, and a convex, rocker-like ground-engaging surface.

In a later approach, as shown in U.S. Pat. No. 4,425,721, there is provided a walking sole to be utilized under an immobilizing bandage of the lower leg, to maintain all foot joints in a rigid condition. The ground-engaging surface thereof is formed in three flat portions, each of which merges into the adjacent portion to form a sole that approaches the normal walking motion.

Problems with such devices as described hereinabove, and with others similar thereto, are created by the lack of recognition that the configuration of the upper, foot supporting surface of a sole is critical to maintaining the foot in a proper post-operative position until healing is complete. Further, and most importantly, in certain types of operations, it is important to relieve the pressure on the operative area which occurs when the weight of the person is placed on the feet. As long as any portion of the foot is engaged thereunder by a portion of the foot supporting surface of the sole, pressure on the foot will occur.

It was therefore to the development of an improved splint which would reduce pressure on the foot while inducing a proper walking motion, that the present invention is directed. It is recognized that some of the prior art devices were relatively successful at improving the walking movement of the post-operative patients; and that some devices aided in retaining the foot in a rigid condition. However, none of the known devices was adequate to accomplish these results, and to eliminate pressure from underneath on the area that had been operated upon.

The present invention is directed to a surgical splint that substantially eliminates pressure on the operative joint, and at the same time encourages a walking motion that is relatively normal. The device accomplishes these objectives through a highly improved design which includes a recess or depression in the foot supporting surface of the sole immediately beneath the operative area that causes the sensitive area to be disengaged or floated from the foot supporting surface of the sole. In a preferred embodiment, the device further includes a ground-engaging surface having a slightly upturned front portion underlying the metatarsophalangeal joint.

Additionally, there is provided an improved upper which is cut slightly higher to help retain the heel of the foot in place, and which is contoured across the dorsum of the foot to relieve pressure from the splint itself.

The overall design is such that the necessity for a cast in addition to the splint is substantially eliminated because it is now possible to "float" the metatarsophalangeal joint, thereby relieving any pressure thereto. As will be detailed below, along with the description of all angles and lines, the splint generally includes a wooden or plastic sole portion with a leather upper. The sole is further provided with an upper, foot-supporting surface and a lower, ground-engaging surface.

The upper surface of the sole includes generally a rear portion for supporting the heel and arch areas of the foot and a forward portion underlying the ball and metatarsal areas of the foot. This upper surface is essentially in the shape of the foot with the rear portion being somewhat narrowed relative to the forward or anterior portion. The outer edges at the heel are slightly elevated to support the heel and prevent lateral rocking thereof. The forward section of the rear portion includes a convex area which supports the arch of the foot.

The anterior portion of the upper surface of the sole includes a recess immediately beneath the areas which were operated on to eliminated pressure and flexing of the metatarsal joint during walking. These areas will generally be described herein as they are designed for splints and adapted for use after surgery to the first metatarsal joint (the big toe). However, the sole can be structured to relieve pressure from any of the other metatarsal joints (the other toes).

The recess is carved out of or molded into the upper surface of the sole, underlying the toe and metatarsal joint of the foot which has been operated upon. The weight or pressure on surrounding portions of the foot is borne by the sole which underlies the ball of the foot and by the convex area which is adjacent the metatarsal recess. This convex area lies adjacent and parallel to the recess, generally along the second and third metatarsals, assuming the recess is beneath the first metatarsal joint.

So designed, the weight of the anterior portion of the foot is supported by the ball and the medial portion of the foot, and the operative area "floats" free of pressure or weight thereto.

While the ground-engaging surface of the sole is designed to aid in walking in a nearly normal manner, it is also designed to require a slight lifting of the foot at each step. This prevents the rolling forward or rocking motion which normally occurs when walking. Elimination of this rocking motion (which prior art devices encourage) further limits pressure on the operative joint.

The angulation of the convex and concave areas are included in the description hereinbelow. It is believed that further modifications and objects of the present invention will become apparent as the detailed description is studied in conjunction with the accompanying drawings, in which.

DETAILED DESCRIPTION OF A PREFERRED EMBODIMENT

Figure 1:
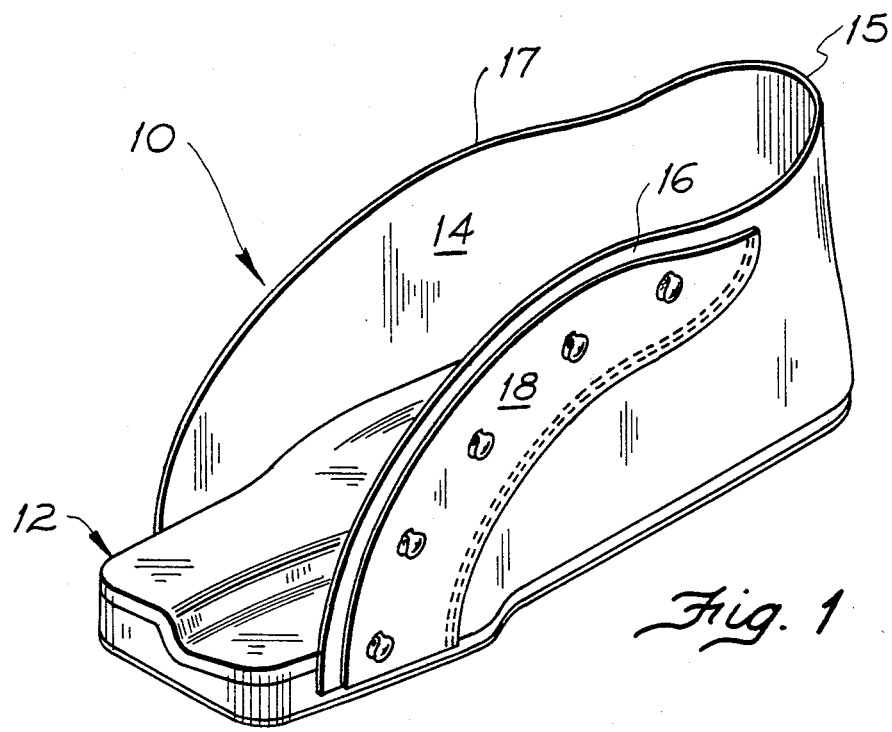
FIG. 1 is a perspective view, looking from the front and inside thereof, of the surgical foot splint according to a preferred embodiment of the invention.
Figure 2:
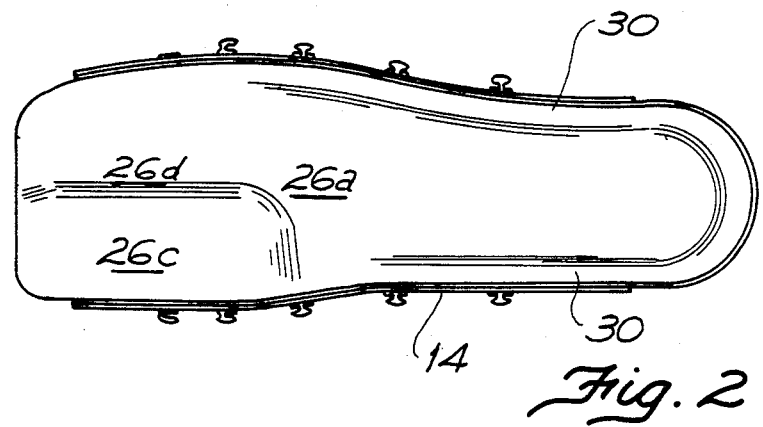
FIG. 2 is a plan view of the splint shown in FIG. 1, illustrating the convex areas in the upper surface of the sole.
Figure 3:
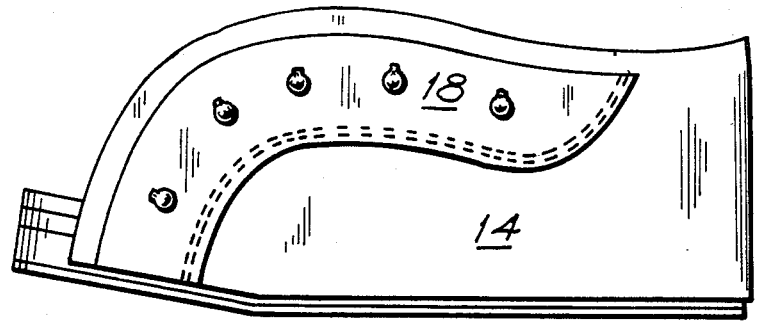
FIG. 3 is a side view of the foot splint illustrated in FIG. 1, showing the angular configuration of the ground-engaging portion.
Figure 4:
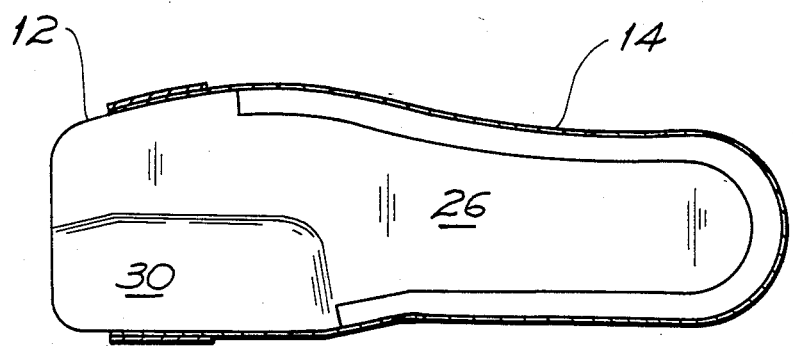
FIG. 4 is a cross-sectional view taken substantially along the lines of 4—4 in FIG. 5.

Turning now to the drawings, and looking first at FIG. 1, the post-operative surgical foot splint 10 generally includes a sole portion 12 and an upper portion 14. The upper 14 is preferably formed of leather for durability, but alternatively may be made of heavy canvas or other flexible material. The splint is held on the foot by the upper 14, which is cut relatively high in areas 15 and 17 to fit just under or around the ankle for better support. In prior art devices the upper has been a singular layer of leather or canvas, cut rather low around the foot. Consequently, when the splint is laced on, there is some likelihood of pressure and discomfort caused by the laces across the instep or dorsum of the foot. In the present invention, the upper 12 includes an inner layer 16 and a partial outer layer 18 which contain the lace eyelets or hooks. Thus, when the splint is laced across the foot, there is a double layer of leather or canvass between the laces and the instep.

Turning now to FIGS. 2-7, there are illustrated plan, elevation, and sectional views which more fully illustrate the aspects of the present invention. For example, in FIG. 2, where a plan view of the upper foot engaging portion of the sole 12 is illustrated, the foot supporting surface 26 includes various areas 26a, 26b, 26c, and 26d. The foot engaging portion 26 is not flat. Rather there is provided a relatively flat heel or posterior portion 26a which supports the heel and area beneath the instep of the foot. The area 26b is convex and actually raised slightly from the surface 26a (see FIG. 5). Also, the area 26d is convex and raised slightly from the surface 26a to support the metatarsophalangeal areas which have not been operated upon, but which are adjacent the metatarsophalangeal area which has been operated upon.

The most important feature of the invention is illustrated at 26c, which is in actuality a depression approximately ¼ inch deep, and for the first metatarsal joint (the big toe), this area is on the inner front portion of the foot engaging portion 26 and is approximately 1½ inches wide and 4 inches long for an average foot. The length of this depression 30 may vary from 3¾ to 4 inches depending upon the size of the foot or shoe. Because of this depression, and also partially because of the convex areas 26b and 26d the metatarsal joint is "floated" or not in engagement with the foot supporting surface 26. This, of course, eliminates any pressure which might otherwise be brought to bear upon the metatarsal joint or the area which has been operated upon. The depression 30 is of such length as to remove pressure from what is considered to be the first ray of the foot. The first ray includes the phalanges, the metatarsal bone, and the cuneiform (the small wedge-shaped bones at the base of the metatarsals).

Figure 5:
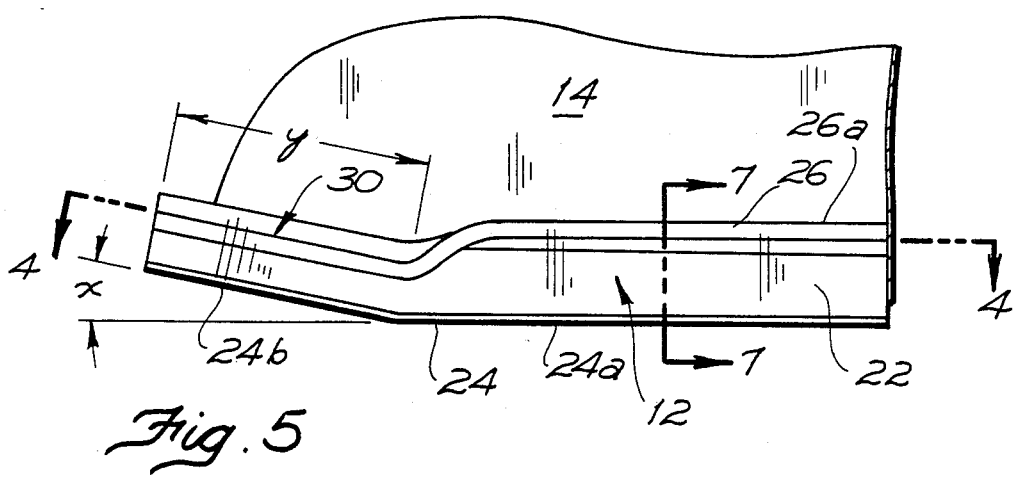
FIG. 5 is a longitudinal cross-sectional view taken substantially along lines 5—5 of FIG. 1.

Looking at FIG. 5, the sole portion 12 includes a central core member 22 which is carved or shaped from wood or molded from plastic and has the same general shape as described hereinabove. A bottom ground-engaging member 24 is applied to the core member 20, which may include rubber tread or other materials conventionally used for ground engaging portions of a shoe or foot splint. The upper surface 26 is some type of leather or fabric lining upon which the foot actually rests. As further illustrated in FIG. 12, the front portion 24b of the ground engaging member (and therefore the core member 22 therebeneath) is tapered upwardly from a point to provide an angle X of approximately 12°. This as described hereinabove, prevents the normal roll of the foot during walking and thus eliminates flexing of the metatarsal joint which would create pain.

Figure 7:
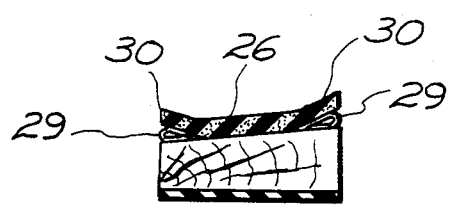
FIG. 7 is a cross-sectional view taken substantially along lines 7—7 of FIG. 5.
Figure 6:
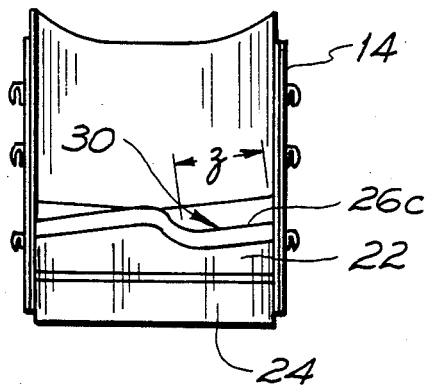
FIG. 6 is a cross-sectional view taken substantially along lines 6—6 of FIG. 5.

Looking at FIG. 7, the rear area 26a of foot engaging portion 26 is inclined upwardly on either side at 30. This is provided by the insertion of small wedge-shaped members 29 between the core member 22 and the edges of the upper foot engaging surface 26. Such a construction prevents the lateral roll of the foot during walking or standing, as well as the longitudinal flexure as described hereinabove.

The upper 14 is stapled, tacked, or otherwise secured to the core member 22 of the sole portion 12. After the core member 22 is formed by a router or other woodworking tools are molded from a polymeric material, the foot engaging layer 26 of orthopedic foam is attached to the upper surface thereof. The undersurface 24 is then trimmed and secured to the core member 22. Finally, the upper 14 is stapled, tacked, glued, or otherwise secured in place.

Such a construction substantially eliminates the need for a cast following certain types of operations on or around the metatarsal joints. The surgical splint of the present invention is utilized to "float" the metatarsal joint which has been the subject of an operation. The shoe is otherwise formed to prevent flexure of that joint during walking and to support the foot more substantially in the areas immediately surrounding the operative joint than beneath the operative joint itself. While the invention is shown as being formed for use in situations where the first metatarsal joint or big toe area has been operated upon, it is obvious that depression 30 could be formed on the other side of the sole portion 12 to float the fifth metatarsal joint, or could be formed intermediate the sides of sole 12 to float any of the second, third, or fourth metatarsal joints.

While a preferred embodiment of the present invention has been described in detail hereinabove, it is apparent that various changes and modifications might be made to the invention without departing from the scope thereof which is set forth in the following claims.

What is claimed is:

1. A post-operative surgical splint for use on a human foot following surgery thereto, said splint comprising:
    (a) a sole having an upper, foot supporting surface and a lower, ground-engaging surface;
    (b) an upper formed of a flexible material and attached to the outer edges of said sole intermediate said upper and lower surfaces thereof for embracing the foot and securing said sole in place;
    (c) means for retaining said upper around the foot;
    (d) said foot supporting surface being comprised of a rear portion for supporting the heel and arch areas of the foot, and a forward portion generally supporting the ball and metatarsal areas of the foot; said forward portion having a depression therein underlying a selected one of the metatarsophalangeal joints of the foot which is desired to be floated as a result of surgery thereto, and convex areas adjacent the sides of and parallel to said depression, said convex areas being raised from the surface of said depression to provide increased support areas immediately surrounding said depression.

2. The post-operative splint according to claim 1 wherein said ground-engraving surface comprises a rear portion generally underlying the heel and arch areas of the foot, and a forward portion generally underlying the ball and metatarsal areas of the foot; said forward portion being tapered forwardly and upwardly from the leading edge of said rear portion to substantially eliminate weight-bearing on the metatarsal area of the foot during walking.

3. The post-operative splint according to claim 2 wherein said tapered forward portion of said ground engaging surface is at an angle of inclination of substantially 12° with respect to said rear portion.

4. The post-operative splint according to claim 1 wherein said upper comprises an underneath layer substantially surrounding and engaging the foot and a partial outer layer which includes eyelets or hooks thereon and to which the shoe strings of said splint are affixed, whereby additional padding is provided between the shoe strings and the instep of the foot.

* * * * *